(12) United States Patent
Ripich et al.

(10) Patent No.: US 11,083,478 B2
(45) Date of Patent: *Aug. 10, 2021

(54) TONGUE CLEANING DEVICE

(71) Applicant: BIO-LIFE INNOVATIONS, LLC, North Canton, OH (US)

(72) Inventors: Robert J. Ripich, Canton, OH (US); David J. Boord, North Canton, OH (US)

(73) Assignee: BIO-LIFE INNOVATIONS, LLC, North Canton, OH (US)

( * ) Notice: Subject to any disclaimer, the term of this patent is extended or adjusted under 35 U.S.C. 154(b) by 122 days.

This patent is subject to a terminal disclaimer.

(21) Appl. No.: 16/261,237

(22) Filed: Jan. 29, 2019

(65) Prior Publication Data

US 2019/0223896 A1 Jul. 25, 2019

Related U.S. Application Data

(63) Continuation-in-part of application No. 15/012,520, filed on Feb. 1, 2016, now Pat. No. 10,188,414.

(60) Provisional application No. 62/110,509, filed on Jan. 31, 2015, provisional application No. 62/264,760, filed on Dec. 8, 2015.

(51) Int. Cl.
 *A61B 17/24* (2006.01)

(52) U.S. Cl.
 CPC ...... *A61B 17/244* (2013.01); *A61B 2217/005* (2013.01); *A61B 2217/007* (2013.01)

(58) Field of Classification Search
 CPC ........... B08B 1/005; B08B 5/04; B25G 1/102; A61B 17/244; A61B 2217/005; A61B 2217/007
 See application file for complete search history.

(56) References Cited

U.S. PATENT DOCUMENTS

| | | | | |
|---|---|---|---|---|
| 5,779,654 | A * | 7/1998 | Foley | A61B 17/244 601/136 |
| 10,188,414 | B2 * | 1/2019 | Ripich | A61B 17/244 |
| 2008/0045988 | A1 * | 2/2008 | Abbott | A61B 17/244 606/161 |
| 2009/0111069 | A1 * | 4/2009 | Wagner | A61M 1/008 433/95 |

* cited by examiner

*Primary Examiner* — Kathleen S Holwerda
*Assistant Examiner* — Brooke Labranche
(74) *Attorney, Agent, or Firm* — McDonald Hopkins LLC

(57) ABSTRACT

A tongue cleaning device includes a tool head defining a trough that delivers the vacuum flow from an inlet to the inner surface disposed above a working edge for efficient removal of debris. The trough has a defined rear wall giving it a defined width. This allows the vacuum flow to be directed to where it is needed to remove debris. One configuration of the device has a head that defines a liquid distribution channel with an outlet disposed in front of the working edge with a supply of liquid being removably in fluid communication with the liquid distribution channel. The liquid supply being a bulk supply or a hand held bottle with a supply tube extending down the handle of the device. Another configuration of the device includes vacuum control openings controlled by the user's finger.

10 Claims, 16 Drawing Sheets

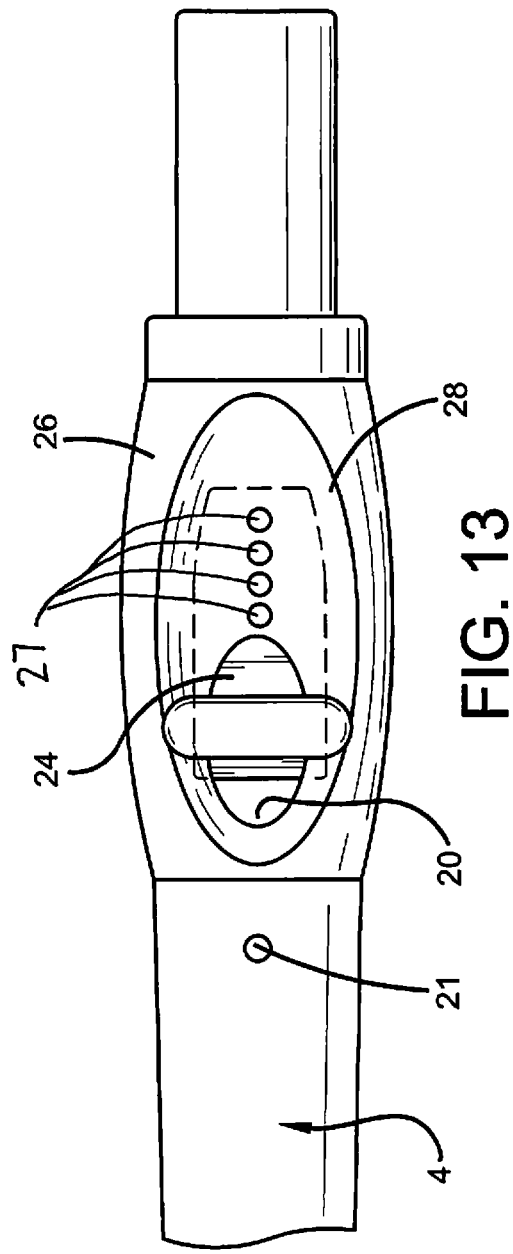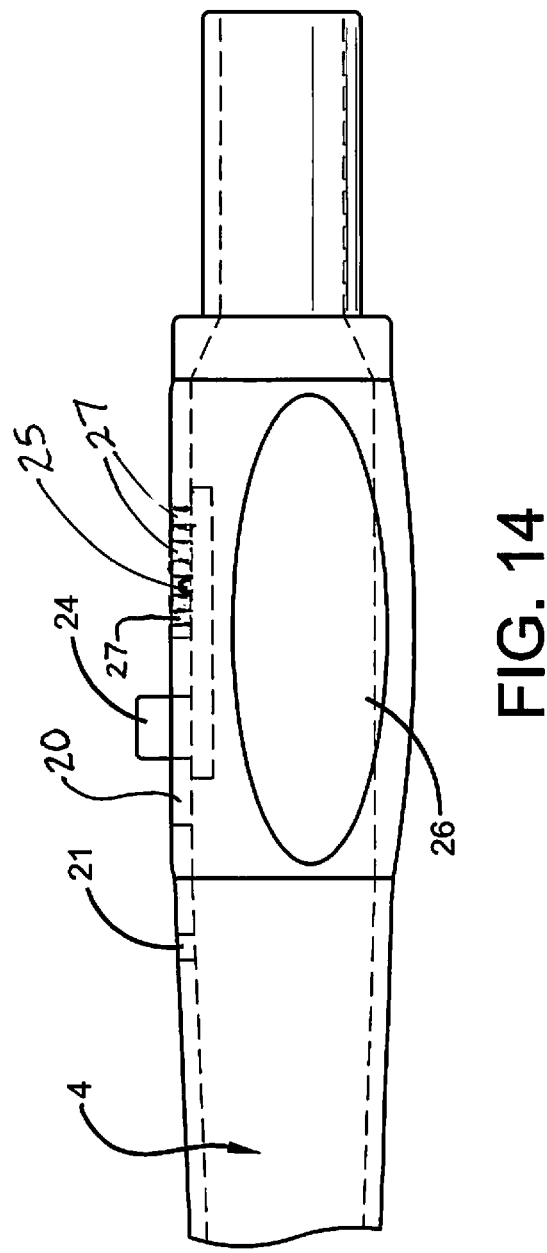
FIG. 13
FIG. 14

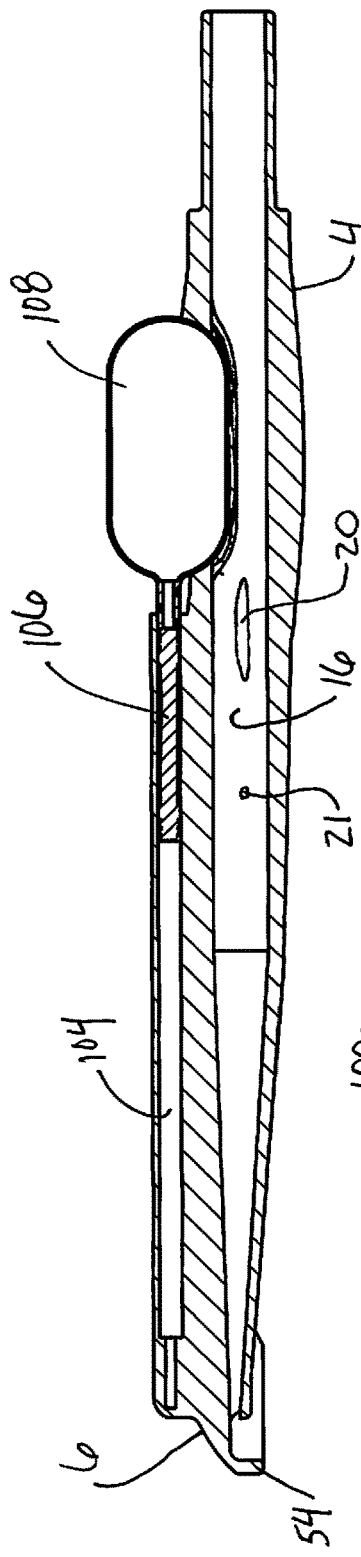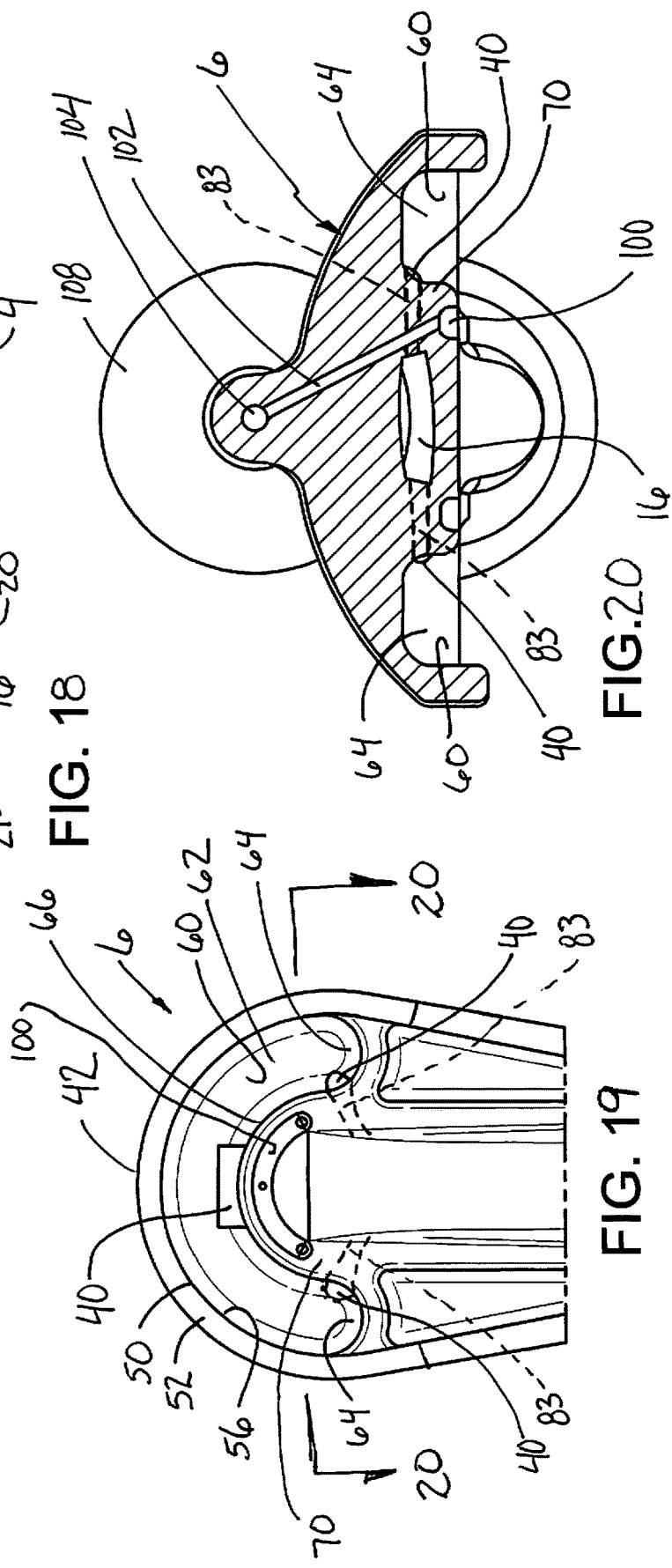

TONGUE CLEANING DEVICE

CROSS REFERENCE TO RELATED APPLICATIONS

This application is a continuation-in-part application claiming priority to U.S. patent application Ser. No. 15/012,520 filed Feb. 1, 2016, U.S. Pat. No. 10,188,414 issued Jan. 29, 2019, which claims the benefit of U.S. Provisional Patent Application No. 62/110,509 filed Jan. 31, 2015, and U.S. Provisional Patent Application No. 62/264,760 filed Dec. 8, 2015; the disclosures of each are incorporated herein by reference. U.S. Design Pat. No. D771,813 issued Nov. 15, 2016, is related to this application.

BACKGROUND OF THE DISCLOSURE

1. Technical Field

The present disclosure generally relates to tongue cleaning devices and, more particularly, to a tongue cleaning device used in cooperation with a vacuum to remove tongue debris from the tool after the tool removes the debris from the tongue. The present disclosure also generally relates to tongue cleaning devices that deposit a liquid solution on the tongue during the cleaning process.

2. Background Information

Numerous types of tongue cleaning devices are known in the art. All have advantages and disadvantages. The art generally desires a tongue cleaning device that effectively cleans the plaque and debris from the tongue while being safe, easy to use, and effective.

One drawback with existing tongue cleaning devices is that the debris collected by the device can fall off of the device shortly after the device is removed from the tongue. Most home users clean their tongues over a bathroom sink and the debris retention problem does not bother them or stop them from using the devices. In other settings, the debris retention problem is of more concern. One such setting is a hospital where it is becoming more desirable to clean the tongues of bedridden patients in order to reduce the amount of bacteria of the patient's tongue. Another situation is a surgical suite wherein the tongue of a patient is cleaned prior to anesthesia. Those who use tongue cleaning devices in these situations desire a tongue cleaning device that will retain or remove the debris from the scraping wall of the tongue cleaning device so that the tongue cleaning device may be easily used on a patient who is lying on his back.

SUMMARY OF THE DISCLOSURE

The disclosure provides a vacuum tongue cleaning device that can be attached and detached from a typical vacuum flow generating tool provided in dental examining rooms, surgical suites, and hospital rooms. The vacuum tongue cleaning device also can be used with a portable vacuum flow generating device for use in nursing home rooms or by home health care providers. The device can use a backflow prevention valve.

In one configuration, the head of the device defines a thin, defined U-shaped trough for receiving and spreading the vacuum flow around the head behind and above the working edge. The trough is disposed parallel to the working edge and has a substantially uniform thickness and depth. The vacuum inlet at the head is disposed at the edge of the trough opposite the working edge of the device. In an exemplary configuration, the top of the trough is disposed above the vacuum inlet. In another exemplary configuration, the vacuum inlet is at least partially defined by the top of the trough. In another exemplary configuration, the inlet is divided between the ends of the trough.

In one configuration, the head of the device defines one or a plurality of liquid or gel distribution channels which have outlets disposed forward of (toward the tip of the device) the working edge of the device. These allow a liquid or gel to be distributed onto the tongue after the working edge and vacuum pass so that the material is not immediately vacuumed off of the tongue. The position of the liquid outlets allows the liquid medicine to be added to the tongue while the papillae of the tongue are freshly agitated and not matted for improved liquid penetration and distribution. If the user wishes to remove all or excess amounts of the liquid or gel, the user moves the device over the area a second time while not distributing the liquid or gel.

The disclosure provides a method for applying a liquid or gel material to the tongue.

The disclosure provides vacuum control opening configurations that allow the user to control the force of the vacuum applied to the head of the device.

The disclosure provides a tongue cleaning device with an integrated supply of material that can be dispensed onto the tongue and then removed with the vacuum. The material is delivered on the handle side of the device to allow it to be vacuumed by the device in the same stroke from the rear to the front of the tongue. The outlet that dispenses the material onto the tongue is provided across a portion of the width of the tongue to apply the material across the tongue.

The disclosure provides a tongue cleaning device that controls the volume of material dispensed onto the tongue.

The disclosure also provides a tongue cleaning device that includes a light disposed to shine on the tongue.

The preceding non-limiting aspects, as well as others, are more particularly described below. A more complete understanding of the processes and equipment can be obtained by reference to the accompanying drawings, which are not intended to indicate relative size and dimensions of the assemblies or components thereof. In those drawings and the description below, like numeric designations refer to components of like function. Specific terms used in that description are intended to refer only to the particular structure of the embodiments selected for illustration in the drawings, and are not intended to define or limit the scope of the disclosure.

BRIEF DESCRIPTION OF THE DRAWINGS

FIG. 13 is a top plan view of another exemplary configuration for the vacuum control defined by the handle.

FIG. 14 is a side view of FIG. 13.

FIG. 18 is a side section view taken along the longitudinal axis of the device of FIG. 17.

FIG. 19 is an enlarged bottom view of the working head of the tongue cleaning device of the FIG. 17.

FIG. 20 is a section view taken along line 20-20 of FIG.

Similar numbers refer to similar parts throughout the specification.

DETAILED DESCRIPTION OF THE DISCLOSURE

Figure 1:
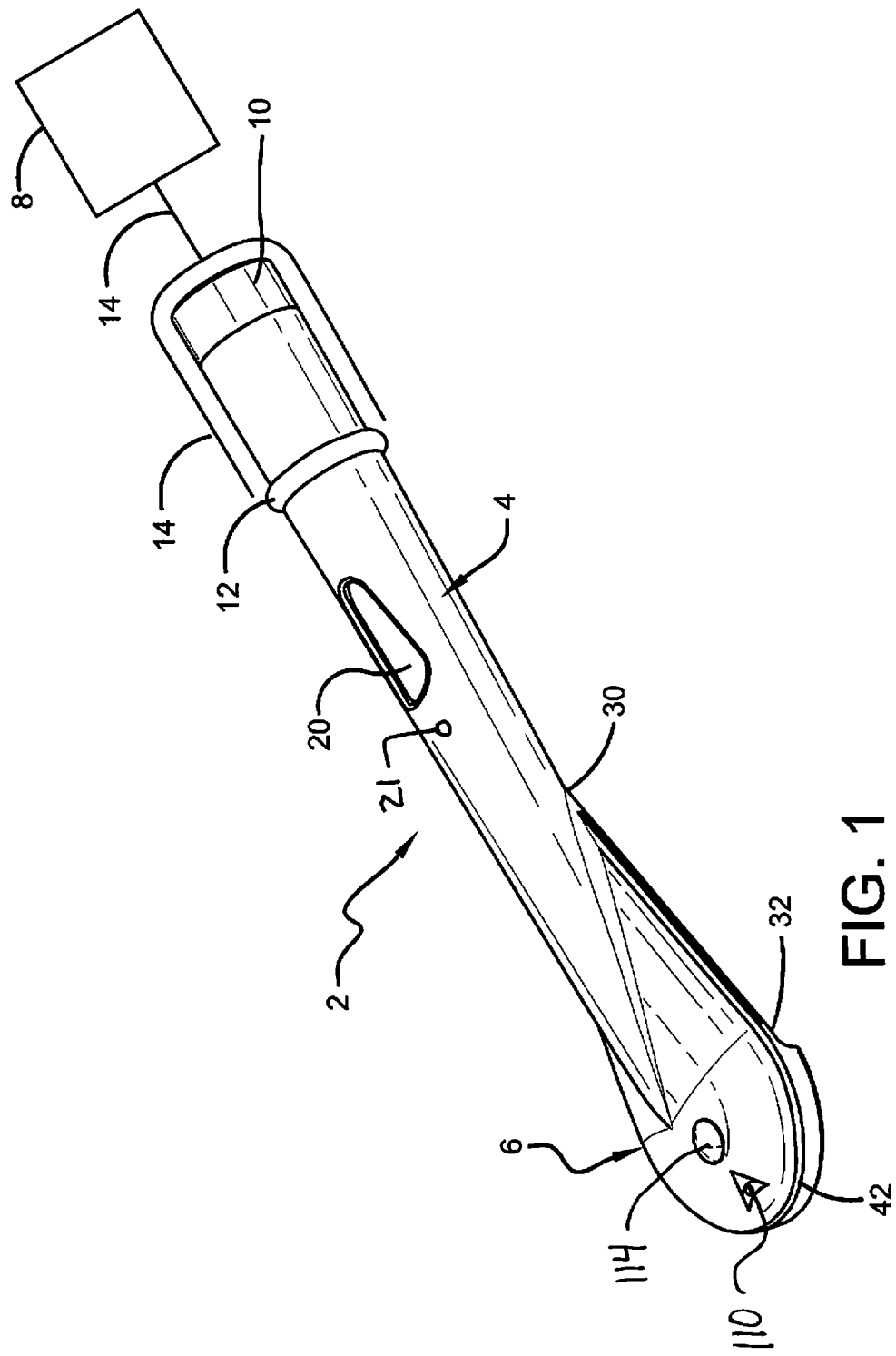
FIG. 1 is perspective view of an exemplary configuration for the tongue cleaning device connected to a vacuum source.
Figure 2:
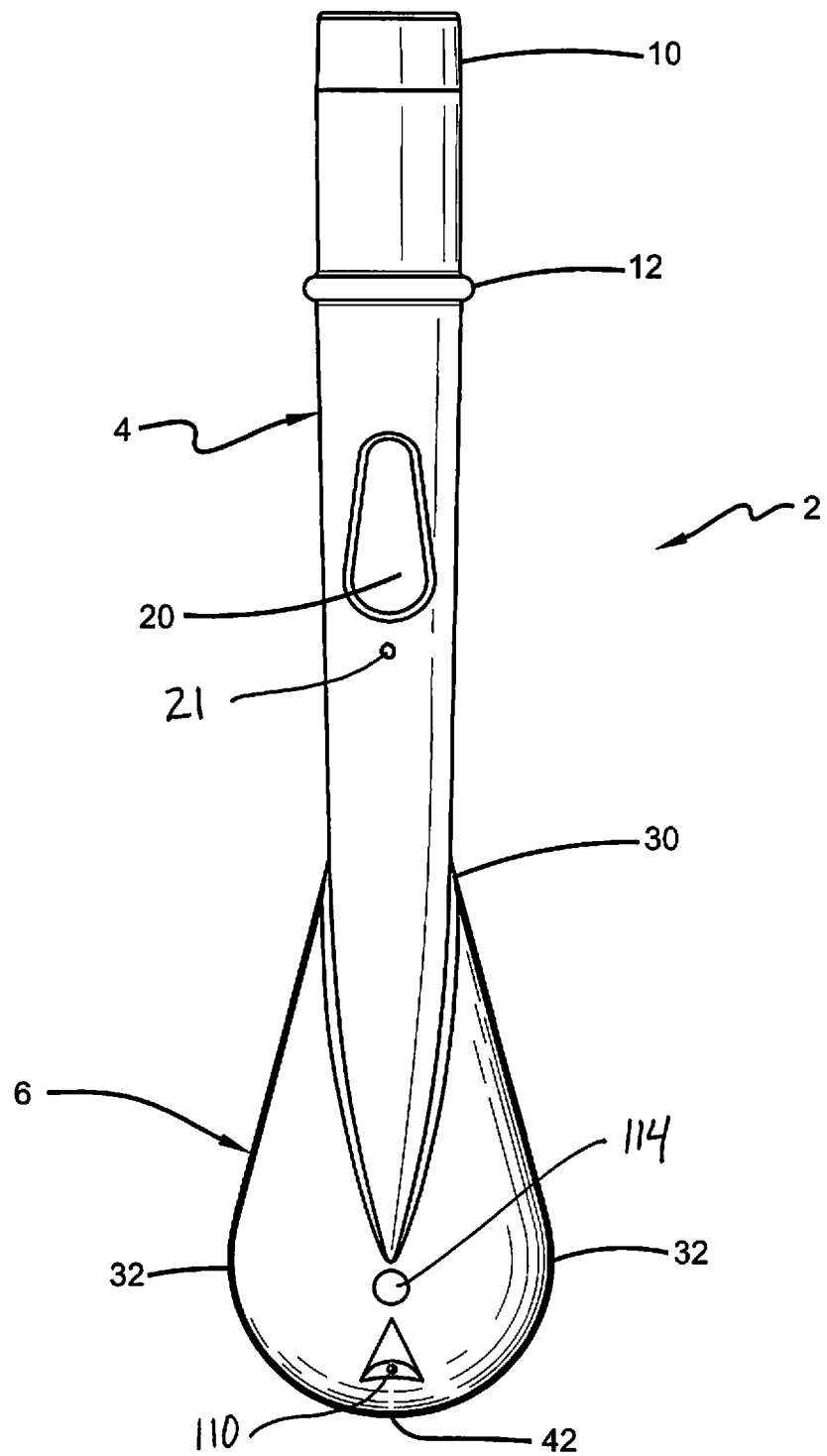
FIG. 2 is a top plan view of the tongue cleaning device configuration depicted in FIG. 1.

The exemplary configurations of a tongue cleaning device are indicated generally by the reference numeral 2 in the accompanying drawings. Each device 2 has a body that defines a passage configured to direct a vacuum flow to a working edge to remove debris from the tool after the tool has removed debris from the tongue. In some of the exemplary configurations, a liquid or gel such as an antibacterial material can be applied to the tongue immediately after or before the cleaning by the working edge. The liquid or gel being applied can be chlorhexidine gluconate, carbamide peroxide, or a mixture of hydrogen peroxide and water. In the following description and drawings, the downward or lower direction is the direction disposed towards (90 degrees to the surface being cleaned) the tongue and the upward direction is disposed directly away from the tongue when the tool is engaging the tongue. The rear of the device is towards the handle while the front is toward the tip of the head. Each configuration of device 2 can be fabricated from any of a variety of rigid materials such as moldable or printable plastics, medical device polymers, ceramics, and/or metals. Each device 2 can be fabricated from titanium. Tool 2 can be fabricated from a material that can be sterilized under high heat.

Each exemplary configuration of device 2 generally includes a handle 4 and a head 6. Handle 4 includes a first end disposed at head 6 and a second end configured to be selectively connected to a vacuum flow generator or vacuum source 8. Vacuum source 8 can be provided in any or a plurality of different ways known in the art. Vacuum source 8 can be a manually-powered squeeze bulb, a manual or powered pump, an electrically-powered vacuum pump typically used in a surgical suite or a dentist's office that includes an air-liquid separator and a waste reservoir to gather liquid and debris, or a source of vacuum flow otherwise powered manually or remotely. Vacuum source 8 is removably connected to the second end of handle 4 with a connection that is substantially airtight so that the vacuum flow does not leak at the connection. The connection is releasable and removable so that device 2 can be readily removed after use and disposed of or cleaned. The removability of the connection allows a single vacuum source 8 to be used with multiple patients by connecting clean tongue cleaning devices 2 as the vacuum source is moved from patient to patient. In the exemplary configuration of device 2, the second end of handle 4 is in the shape of a hollow cylinder with one end slightly tapered 10 and the other end bounded by a rounded flange 12. The tapered end 10 allows device 2 to be slid into the end of a vacuum tube 14 and flange 12 creates a stop for the vacuum tube 14. Device 2 is secured by friction and by the vacuum force applied by the vacuum tube 14.

Figure 3:
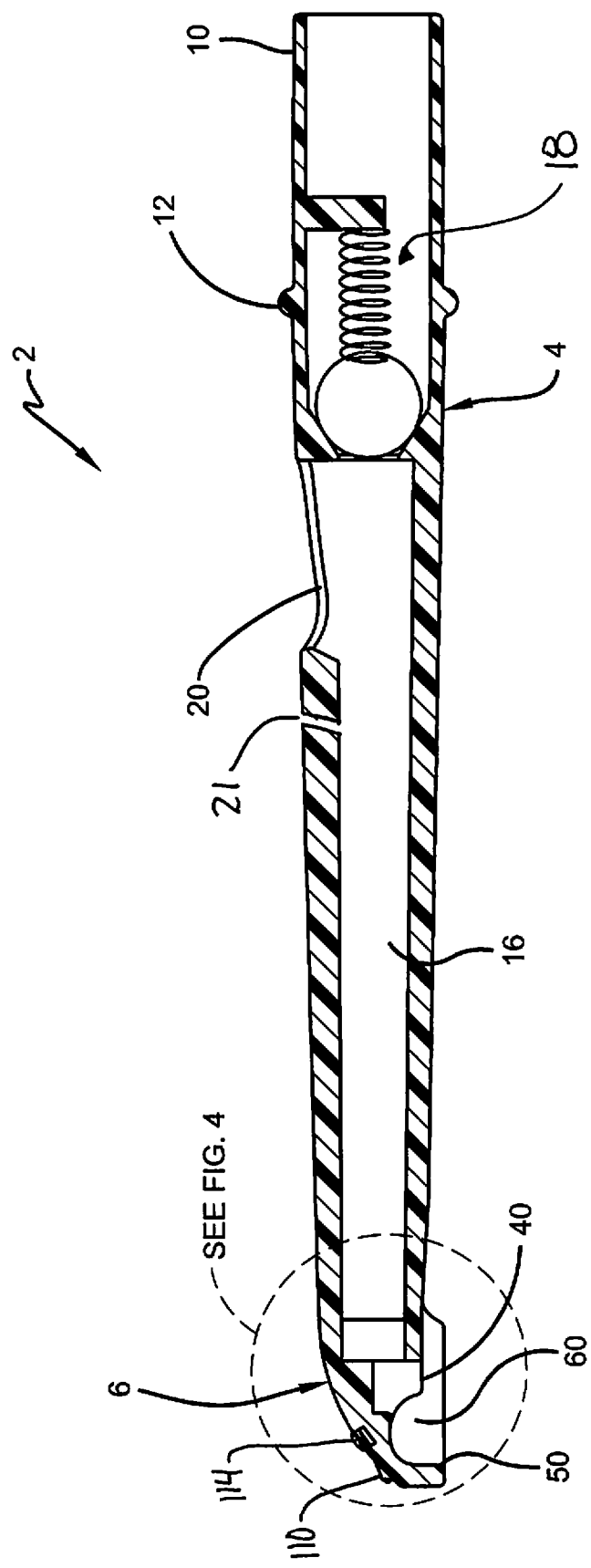
FIG. 3 is a side section view taken along the longitudinal axis of the device of FIGS. 1 and 2.

Handle 4 defines the vacuum passage 16 that directs the vacuum flow supplied by vacuum source 8 through the body of device 2. A backflow preventer valve 18 is optionally provided along vacuum passage 16 to minimize the risk that vacuumed saliva and debris present in tube 14 would flow back into a newly-installed device 2. A biased ball check valve is depicted in FIG. 3 but resilient flexible flap valve or other backflow prevention device can be used.

A primary vacuum control opening 20 is defined by a portion of handle 4. As shown in FIG. 1, primary vacuum control opening 20 can be defined by the upper surface portion of device 2 such that a user's index finger can be positioned over at least a portion of vacuum control opening 20 when the user is holding device 2 in the same manner as one holds a knife or fork when pushing down with an index finger. In this case, the index finger of the user can push down on device 2 but can also control the strength of the vacuum applied to head 6. When the user wants a stronger vacuum force applied to head 6, the user covers the entire vacuum control 20 opening. When the user wishes to lessen the vacuum force, the index finger can slide to expose portion of vacuum control opening 20 to allow some of the vacuum force to be delivered to vacuum control opening 20 instead of head 6. A secondary vacuum control opening 21 can be provided in front of vacuum control opening 20 or at another location on head 6 or handle 4 to ensure the vacuum flow through handle will always have an unsealed vacuum inlet in the unlikely occurrence that head 6 is pushed down to where it could vacuum seal to the tongue. As long as secondary control opening 21 is not covered by the user, device 2 cannot entirely vacuum seal to the tongue.

Figure 8:
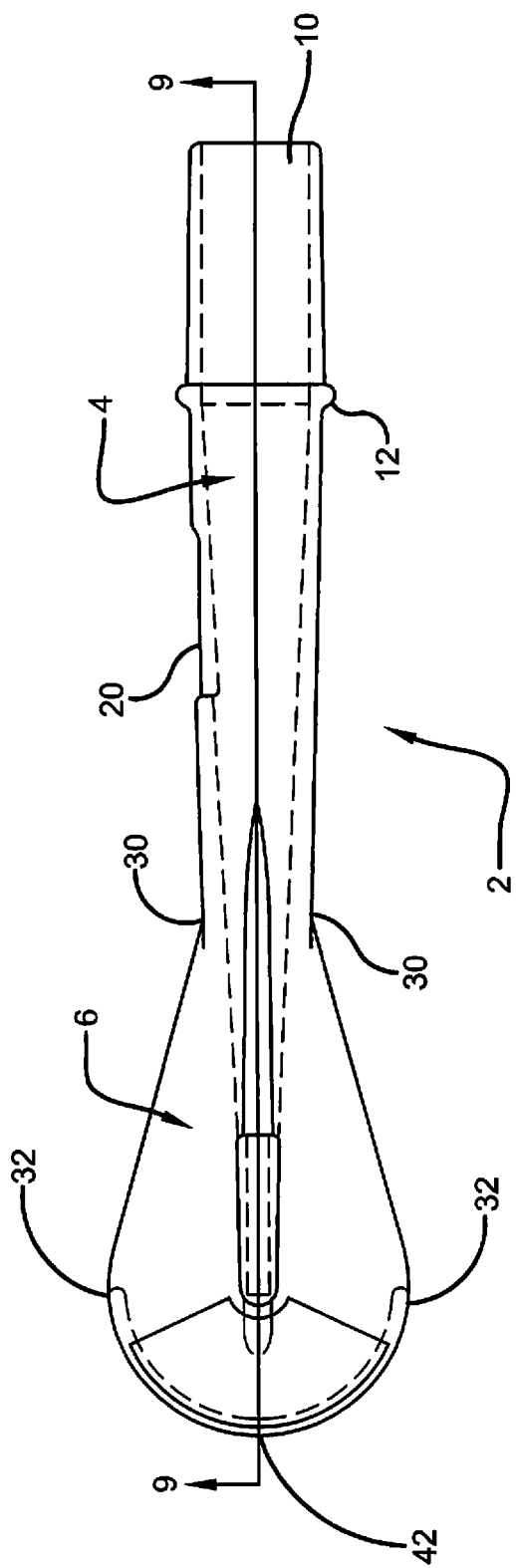
FIG. 8 is a top plan view of another exemplary configuration for the tongue cleaning device of this disclosure.
Figure 9:
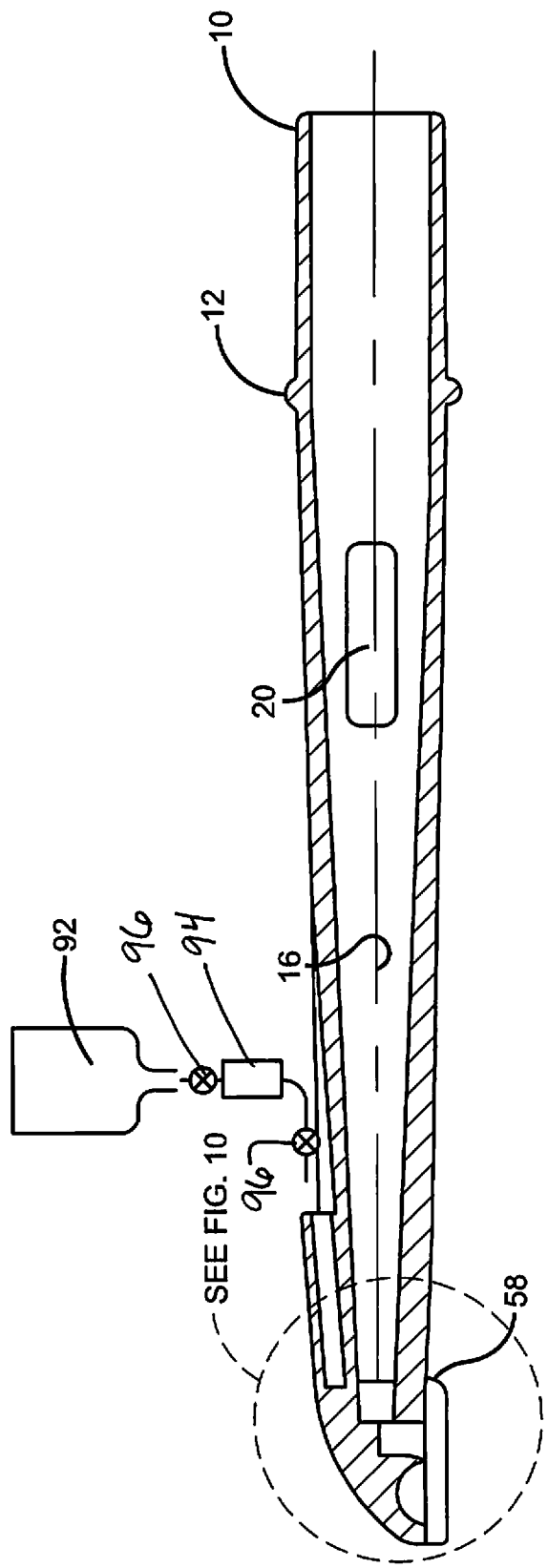
FIG. 9 is a section view taken along line 9-9 of FIG. 8.

In the exemplary configuration of FIGS. 1-5, vacuum control opening 20 is tear drop-shaped to provide a wider range of control than would be provided by a control opening shape having a constant width such as the vacuum control opening 20 depicted in FIGS. 8-9. Positioning the narrow end of the tear drop-shaped vacuum control opening 20 closest to the palm of the user's hand (the second end of the handle) allows a slight amount of vacuum pressure to be released by sliding the user's index finger forward towards head 6. This configuration ensures the user retains good control over head 6 as well having good control over the vacuum source. In this configuration, secondary vacuum control opening 21 is depicted through the top of handle 4 but it can be located anywhere along handle 4.

Figure 6:
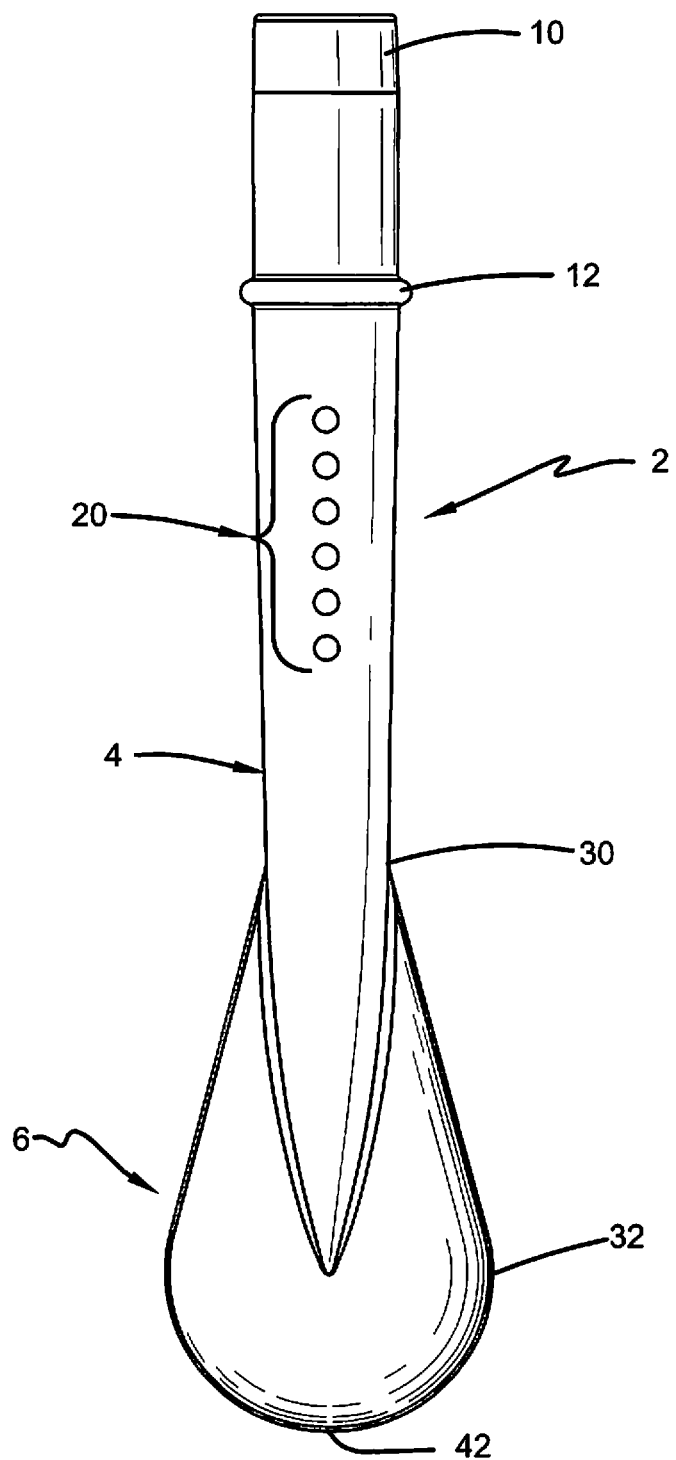
FIG. 6 is a top plan view of another exemplary configuration for the tongue cleaning device of this disclosure.
Figure 12:
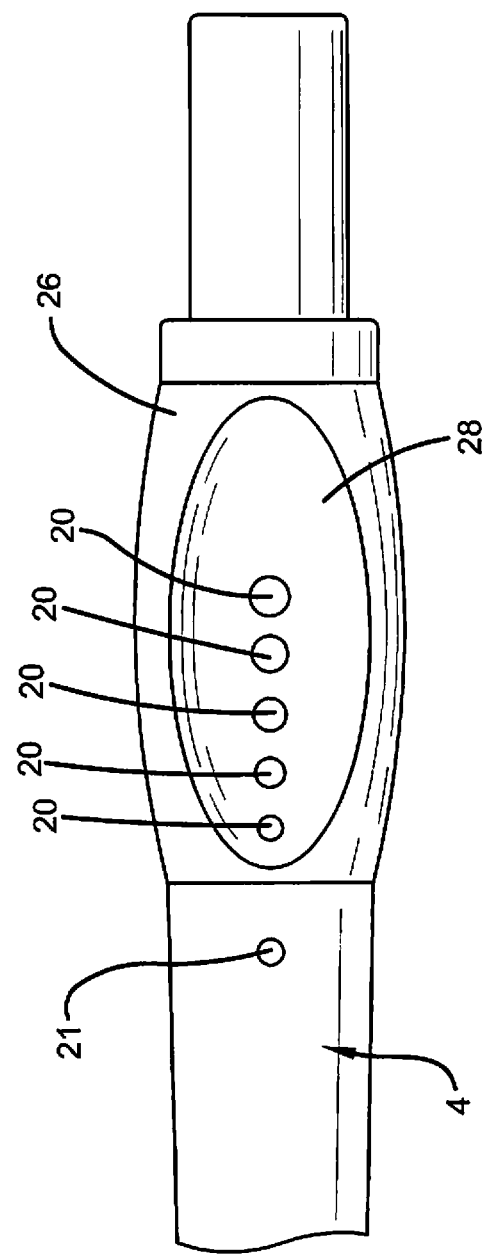
FIG. 12 is a top plan view of another exemplary configuration for the vacuum control defined by the handle.

In the exemplary configurations of FIGS. 6 and 12, a plurality of vacuum control openings 20 are defined along the longitudinal axis of the handle. These openings 20 are disposed close together (such as providing a plurality of openings disposed within a half inch space) so that a user's finger can cover a plurality of openings 20 and then be slid in one direction or another to expose one opening at a time or a plurality of openings 20 at a time to relieve vacuum force. The openings can be the same size or different sizes. In the configuration of FIG. 12, the openings are smaller close to the head and progressively get larger. For example, the opening closest to head 6 may be 1 mm in diameter while the opening 20 farthest from head 6 can have a diameter of 4 mm with the plurality of openings 20 between the two ends being evenly sized. In the example with five openings, the second opening has a diameter of 1.75 mm, the middle opening diameter is 2.5 mm, and the fourth opening is 3.25 mm. In the configuration of FIG. 6, secondary vacuum control opening 21 is not depicted but can be disposed on the front, side, or bottom of handle 4.

Figure 15:
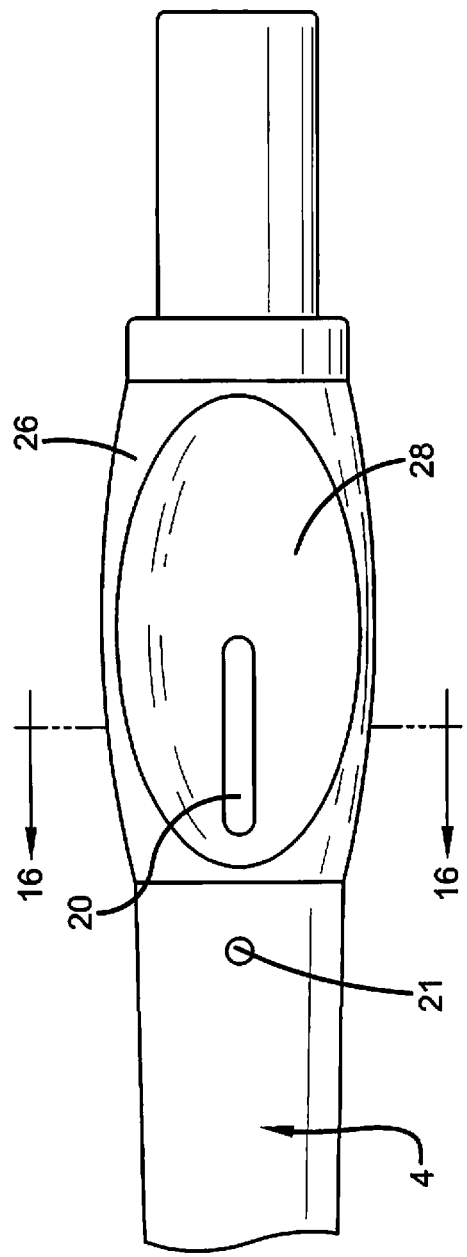
FIG. 15 is a top plan view of another exemplary configuration for the vacuum control defined by the handle.
Figure 16:
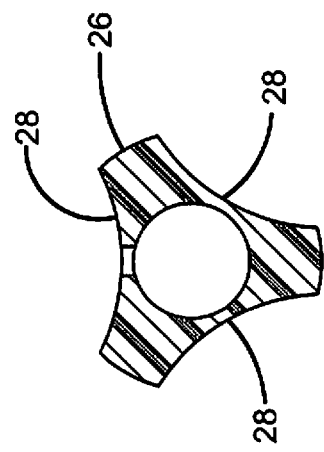
FIG. 16 is a section view taken along line 16-16 of FIG. 15.
Figure 17:
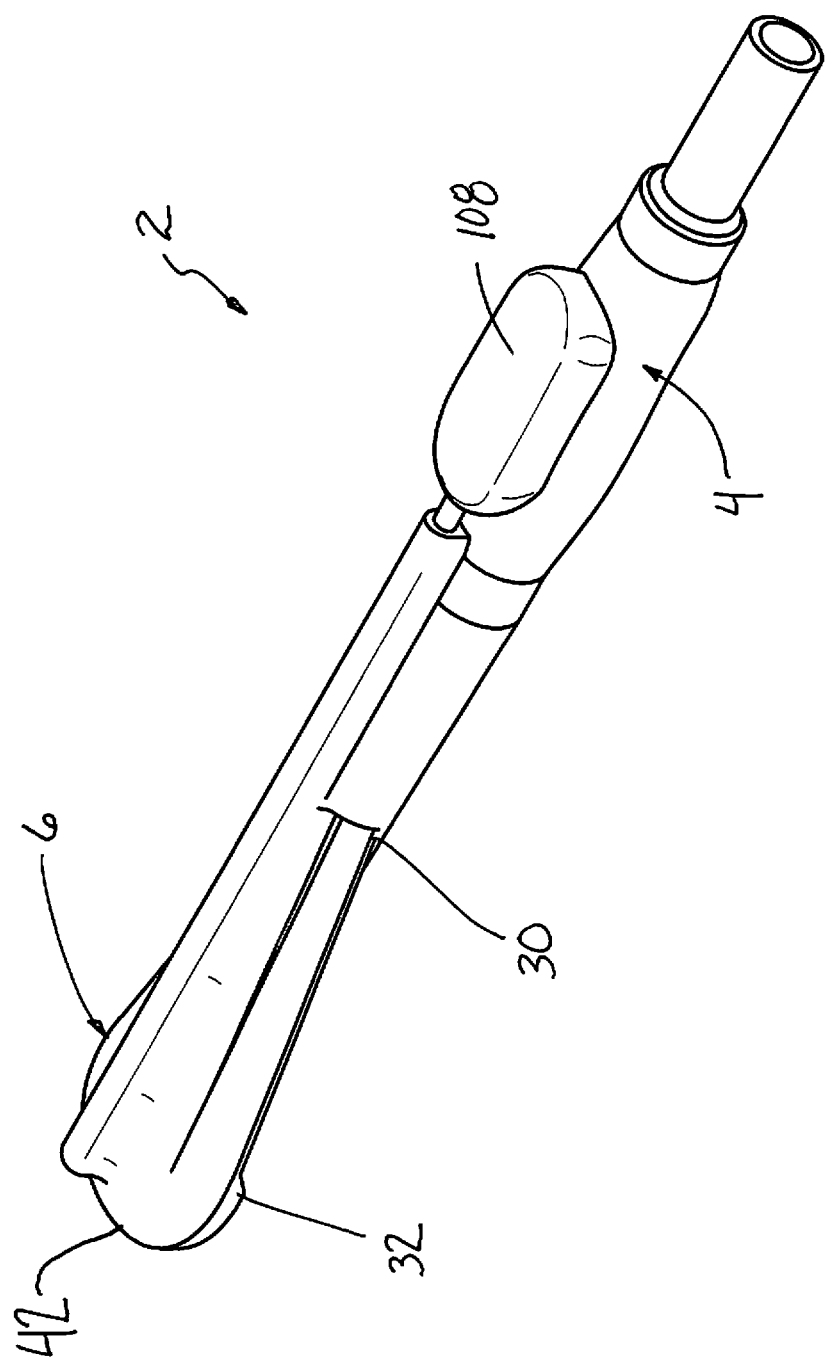
FIG. 17 is a perspective view of another exemplary configuration for the tongue cleaning device of this disclosure.

In the exemplary configuration of FIGS. 8-9, a single opening 20 is disposed on the side of handle 4 and could be controlled by the user's middle finger. In the exemplary configuration of FIG. 15, opening 20 is provided in the form of an elongated slit. The slit can be about 8 to 12 mm long and 1 to 4 mm wide. This slit allows the user to control the vacuum delivered to the head 6 of device 2. The configuration of FIG. 8 can be a slit of the same size. A benefit with the slit is that it is substantially thinner than the user's finger and thus easy to find and seal with the finger.

In the exemplary configuration of FIGS. 13-14, a sliding cover 24 is provided to selectively close vacuum control opening 20. Sliding cover 24 is carried by handle 4 and can be slid back and forth by the user's finger to open and close opening 20. An advantage with cover 24 is that the user can change the position of his fingers without changing the vacuum force. A locking tooth 25 is received in one of a plurality of recesses 27 to hold cover 24 in place until intentionally moved by the user. Tooth 25 can be carried by cover 24 or by handle 4.

Figure 7:
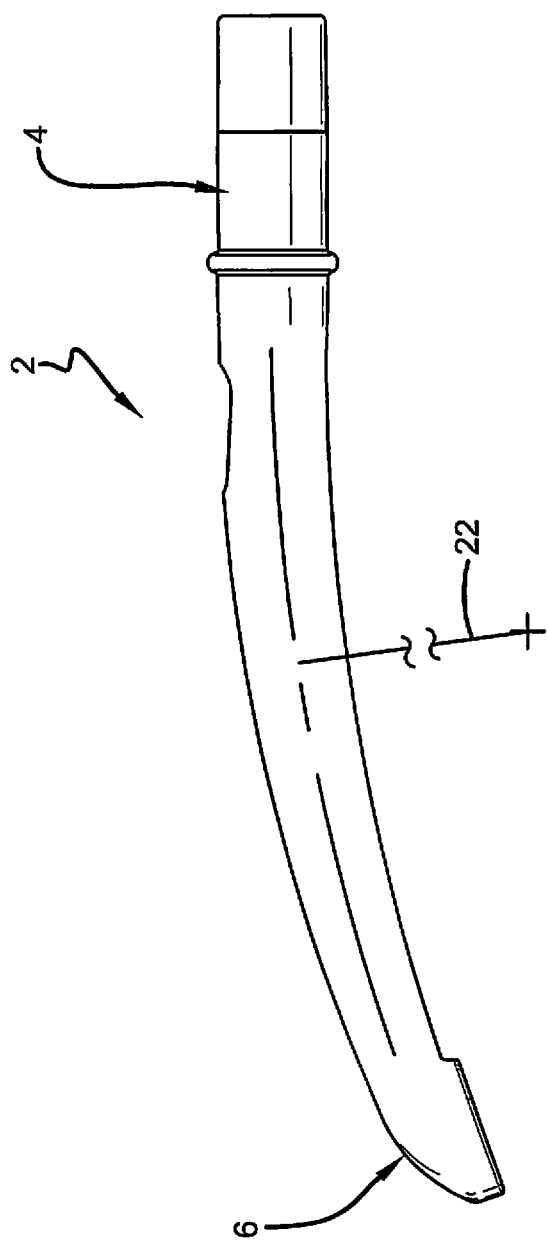
FIG. 7 is a side view of another exemplary configuration for the tongue cleaning device of this disclosure.

In the exemplary configurations depicted in FIGS. 1-4 and 8-9, the longitudinal axis of the handle is substantially straight. In another configuration, a portion of handle 4 curved such that it has a radius 22. An example of this configuration is shown in FIG. 7 wherein handle 4 is curved when viewed from the side. Using a generally curved handle allows the working head of device 2 to easily reach the rear of the tongue especially when the user's mouth is not fully open or when other implements are disposed in the mouth (such as a breathing tube). Radius 22 can be in a range of three to twelve inches.

In the configurations of FIGS. 12-16, handle 4 has an enlarged grip area 26 that defines opening 20 or openings 20. As shown in cross section, grip area 26 defines three recesses 28 that receive the user's thumb and two fingers for added control over device 2. Opening 20 or openings 20 are defined by handle 4 within one or more of these recesses 28 which helps the user's finger to selectively cover openings 20 to control the vacuum. As shown in the drawings, opening 20 or the group of openings 20 are not centered within recess 28. They are positioned forward toward head 6 such that the user can grip the rear of recesses 28 without covering opening 20 or openings 20. As such, each recess 28 has a forward portion and a rear portion with at least one of recess 28 defining opening 20 in at least the forward portion of recess 28. In some of the configuration, the entire opening 20 can be in the forward portion of recess 28. In other configuration, opening 20 can extend into the rear portion.

The vacuum flow applied to head 6 can have a measured vacuum strength from about 0.25" to 7.00" Hg Gauge vacuum at standard temperature and pressure. About 1.00" to 2.00" Hg Gauge vacuum is a desirable range. As such, device 2 can be configured with vacuum control opening 20 and secondary vacuum control opening 21 to cooperate to provide for a minimum of 0.25" Hg applied to head 6 when openings 20 and 21 are completely uncovered even when a vacuum pressure of 7.00" Hg is applied to handle end 10. When opening 20 is completely covered, most of the 7.00" Hg vacuum pressure is applied to head 6 with opening 21 providing a safety against vacuum sealing head 6 to the tongue.

In the exemplary configurations, head 6 is integrally connected to the first end of the handle 4 and vacuum passage 16 of the handle extends into head 6. Head 6 tapers outwardly from a first end 30 having a width equal to the portion of handle 4 where head 6 joins with handle 4 to a middle portion defining a maximum width 32. The maximum width location is disposed intermediate the inlet 40 to vacuum passage 16 and the first end of handle 4. This is so that inlet 40 is forwardly positioned within a closed head. The outermost end 42 of head 6 is smoothly rounded between these two maximum width dimension points 32.

Figure 4:
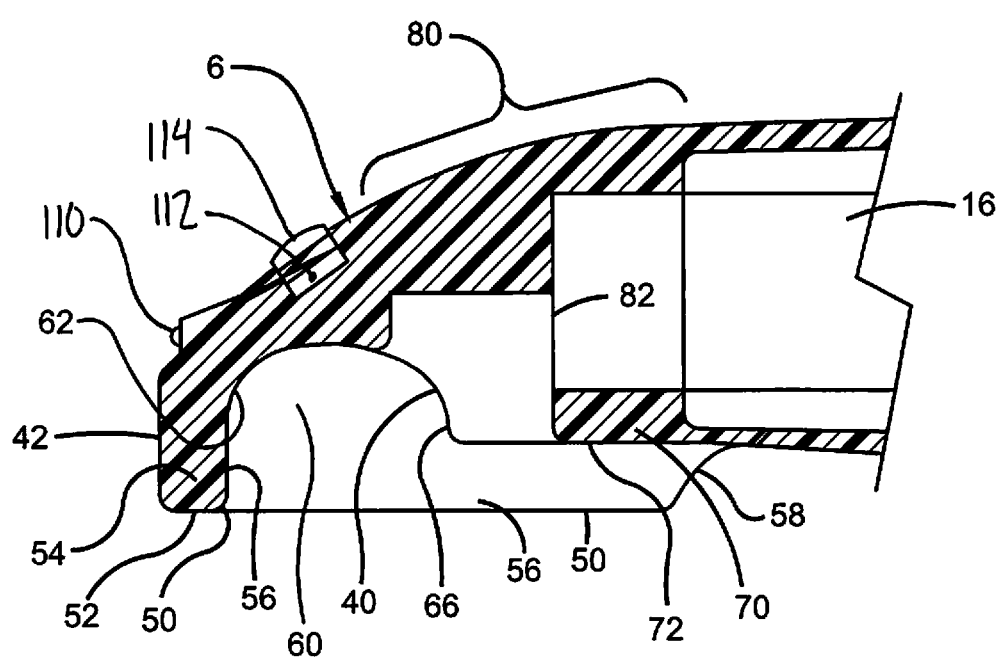
FIG. 4 is an enlarged view of the encircled portion of FIG. 3.
Figure 5:
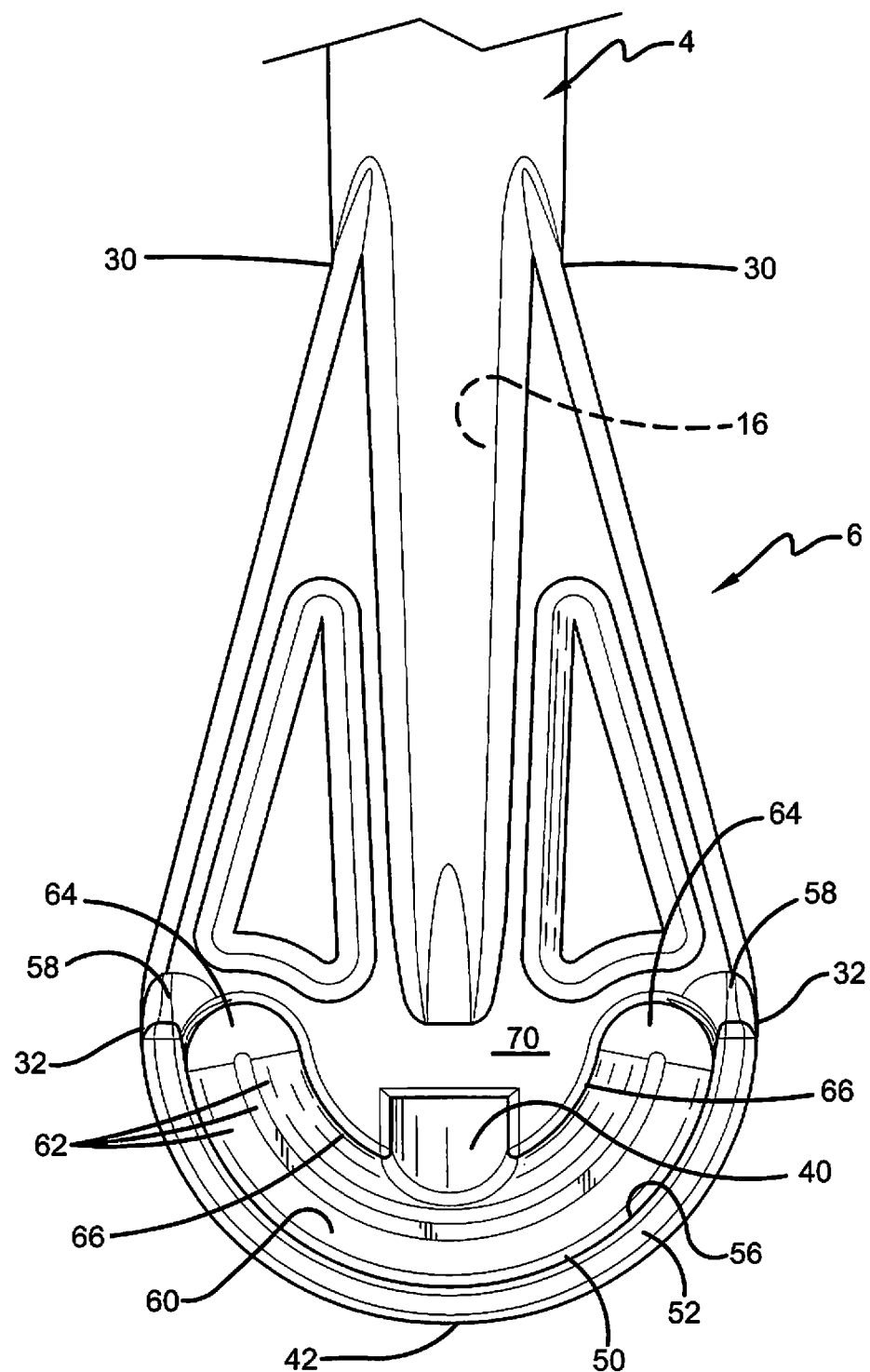
FIG. 5 is an enlarged bottom view of the working head of the tongue cleaning device of the FIG. 1 configuration.
Figure 10:
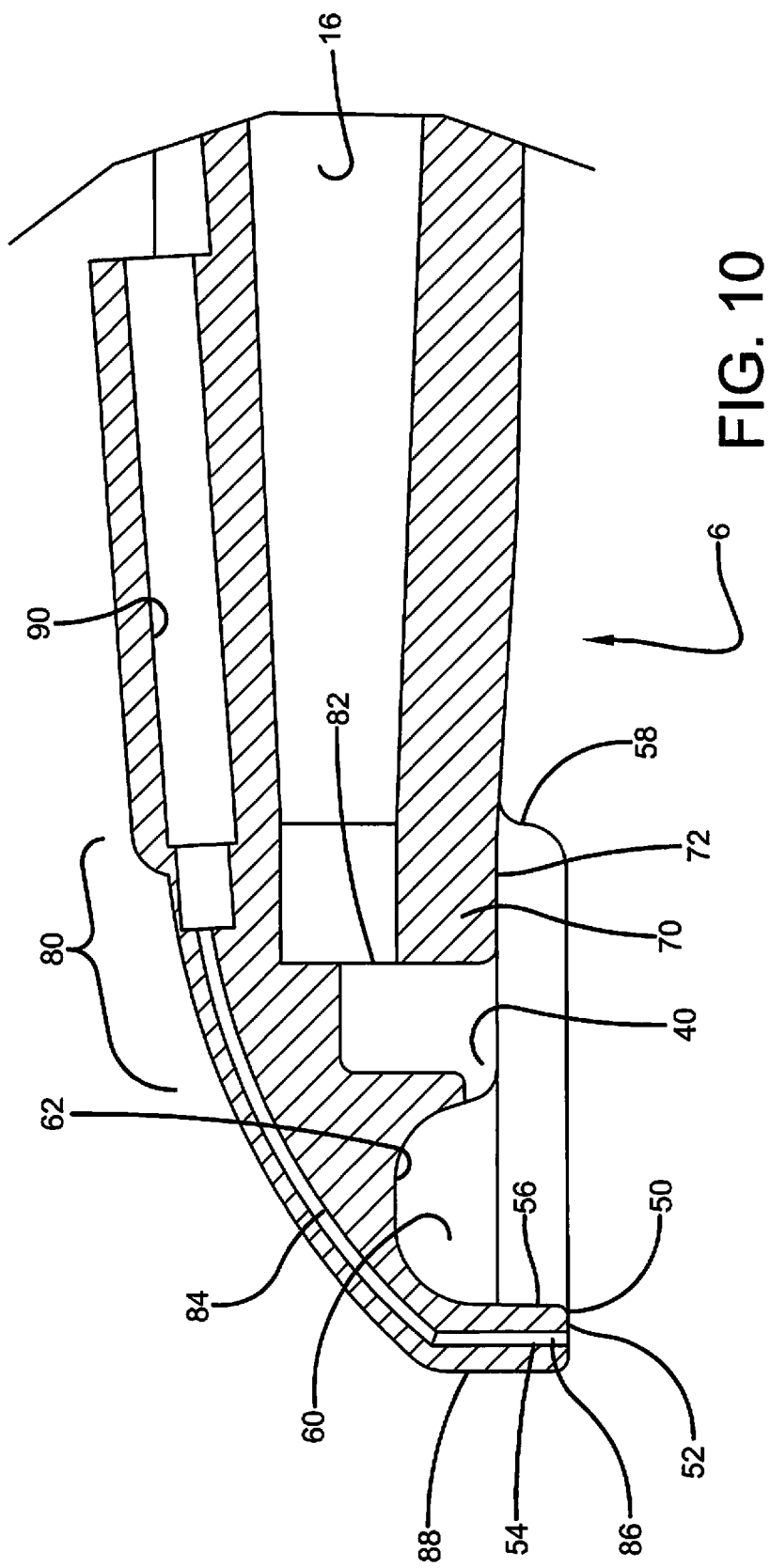
FIG. 10 is an enlarged view of the encircled portion of FIG. 9.
Figure 11:
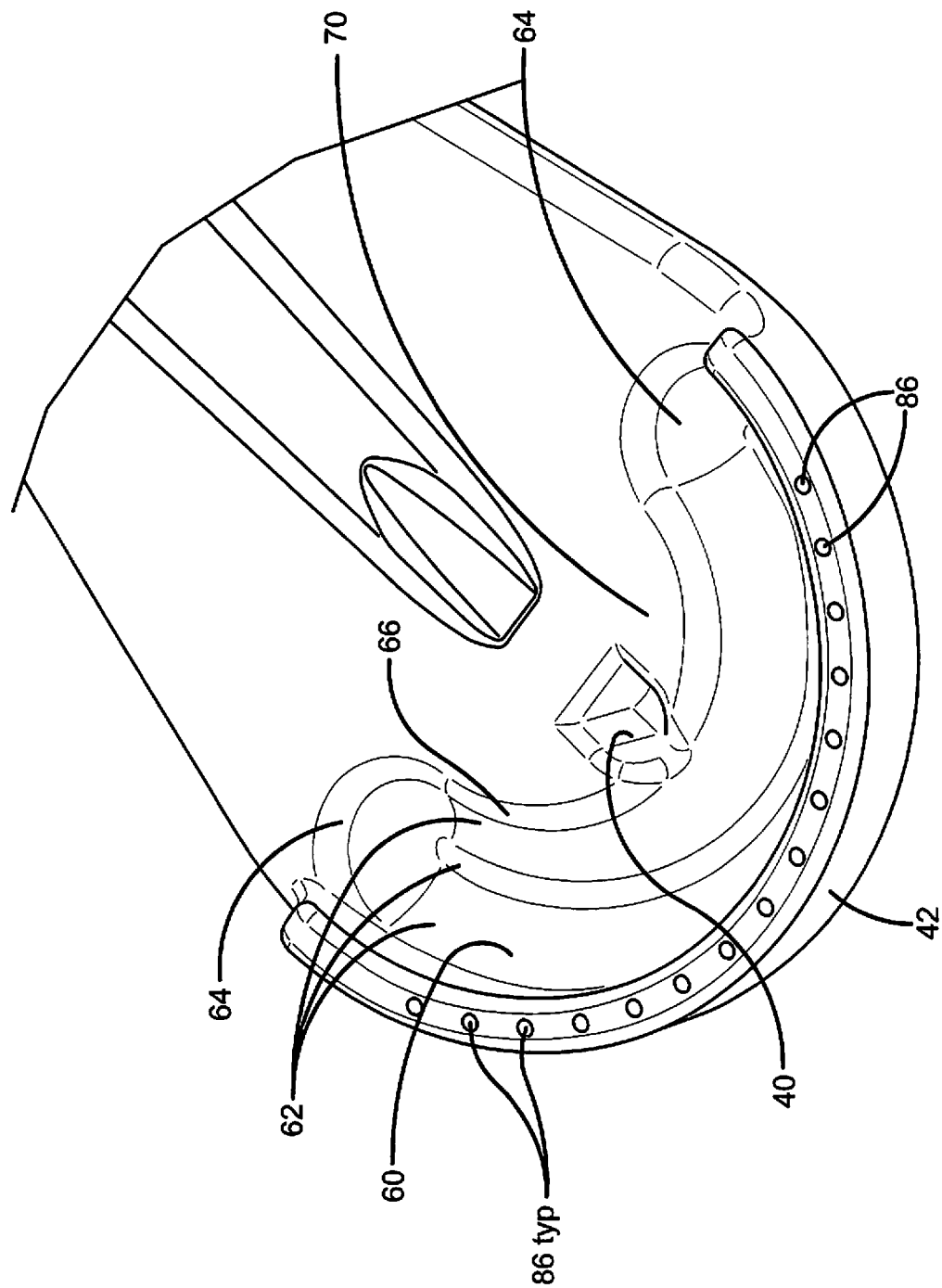
FIG. 11 is a perspective view of the bottom of the working head of the exemplary configuration of the tongue cleaning device of FIG. 8.

Head 6 includes a working edge 50 defined at the junction or corner of a bottom surface 52 of a scraping wall 54 and an inner surface 56 of wall 54. This corner is rounded to avoid damaging the tongue. Exemplary radii for this working edge are disclosed in U.S. Pat. No. 7,029,484 which is incorporated herein by reference. When working to remove debris from the tongue, working edge 50 engages the tongue and inner surface 56 extends upwardly from the tongue. Debris and saliva are gathered on inner surface 56 when working edge 50 engages the tongue surface and moved along the tongue surface with some downward pressure. Working edge 50 and inner surface 56 extend along a curve that substantially defines a half circle (when viewed from below) from middle portion 32 on one side of head 6 to middle portion 32 on the other side of head 6. Working edge 50 and inner surface 56 define an arc of 120 degrees to 180 degrees when viewed from the bottom of device 2 as shown in FIGS. 5, 11 and 19. The rear ends of working edge 50 are thus disposed behind inlet 40. Working edge 50 is disposed lower than the bottom of the central portion of head 6 and the front half or head-end of handle 4 (when handle 4 is horizontal) as shown in FIGS. 4 and 10 wherein working edge 50 is stepped down (at reference numeral 58) from head 6 to allow working edge 50 to engage the tongue free of interference from head 6 and handle 4. Working edge 50 can have a flat lower surface or a curved lower surface shaped to engage the tongue such as the concave configuration depicted in FIG. 26 of U.S. Pat. No. 7,029,484 or a convex configuration wherein scraping wall 54 has a maximum height at outer or front end 42 of head 6. Working edge 50 can be angled when viewed from the side such that the center portion of working edge 50 is disposed lower than its rear ends. Working edge 50 can be defined to match the shape of a tongue with dual curves.

Head 6 defines a trough 60 disposed along a majority of inner surface 56 which is disposed above working edge 50. Trough 60 is disposed above inner surface 56 and has a defined width and depth. The defined width helps device 2 function at different angles because a portion of the vacuum flow is delivered through trough 60 regardless of the angle of head 6. A deeper trough 60 allows for better containment of debris while a shallower trough 60 provides for a wider range of approach. Trough 60 directs the vacuum flow to inner surface 56 and allows the mix of debris and saliva to be efficiently removed from inner surface 56 by the vacuum flow through device 2. Trough 60 is defined by a curved top wall 62 that smoothly joins with inner surface 56 free of any steps of ledges where the vacuum flow would be interrupted or where debris would gather. Curved top wall 62 can be provided in a front curved quarter, a central flat portion, and a rear curved quarter. In one configuration, the top of wall 62 can be disposed higher than the uppermost portion of vacuum inlet 40. In another configuration, a portion of vacuum inlet 40 is defined by top wall 62. The ends 64 of trough 60 can be smoothly rounded. Ends 64 are disposed behind inlet 40. Trough 60 is also partially defined by a rear surface 66 disposed substantially concentric with inner surface 56 to define the width of trough 60. Rear surface 66 extends between ends 64 and along the rear of each end until reaching inner surface 56. Rear surface 66 is interrupted by inlet 40. Rear surface 66 can be vertical and parallel with inner surface 56 or can be angled towards the rear of device 2. Rear surface 66 does not extend down as far as inner surface 56 but functions to limit leakage of the vacuum from the rear of head 6. Rear surface 66 is defined by a central wall 70 of head 6. Rear surface 66 defines the constant width of trough 60.

Central wall 70 defines inlet 40. As shown in FIGS. 4-5 and 10-11, inlet 40 is defined by portions of rear surface 66 as well as top wall 62 of trough 60. Inlet 40 also has a portion that opens through the bottom surface 72 of central wall 70. This configuration distributes the vacuum flow evenly throughout trough 60 and provides for some vacuum under the central portion of head 6. Surface 72 prevents the vacuum from being delivered to an entirely open lower surface of head 6. Extending inlet 40 through top wall 62 delivers a portion of the vacuum flow directly to the top curved wall of trough 60 which allows the vacuum to be delivered quickly to inner surface 56 with a minimum of turns and obstacles. Bottom surface 72 is disposed above working edge 50 to minimize the likelihood device 2 will become stuck to the tongue when in use.

Head 6 defines an inlet tube 80 between inlet 40 and the end of vacuum passage 16. In order to decrease the chance of clogging and in order to increase the removal efficiency of device 2, inlet tube 80 has a throttle 82 which is an area of decreased cross sectional area in order to speed up the vacuum flow. A plurality of throttles 82 can be used. In this configuration, inlet tube 80 increases the speed of the vacuum flow after the flow enters inlet 40. The speed is then decreased prior to entering vacuum passage 16. The decrease in area is substantial and is forty to sixty percent in the exemplary configuration. The transitions can be abrupt in order to interrupt laminar flow. In the exemplary configuration, a pair of chambers define inlet tube 80 with the smallest opening 82 of the vacuum passage being defined between the two chambers. The outermost chamber that defines inlet 40 allows debris and saliva to be gathered prior to being subjected to increase in velocity through the necked down section between the two chambers. In other configurations, a single chamber can be used. In other configurations, the transitions can be smooth in order to maintain laminar flow. The increase in the speed of the flow helps lift debris and saliva up into the vacuum passage when device 2 is in use.

In an alternative configuration depicted in FIGS. 19 and 20, inlet 40 is located at trough end 64. Inlet 40 can be located at one trough end 64, at both trough ends 64, and these can be used with or without the centrally-located inlet 40. Branch vacuum pathways 83 are defined by central wall 70 and are in fluid communication with vacuum passage 16. Locating inlets 40 at ends 64 helps remove liquid from the edges of the tongue. Inlets 40 can be disposed through top wall 62, rear surface 66, ends 64 or a combination of these surfaces.

In the exemplary configuration of FIGS. 8-11, device 2 includes a fluid distribution channel 84 defined by head 6 that allows the user to distribute a substance such as a liquid or gel antibacterial agent, a medicine, or a freshener agent to the tongue directly after working edge 50 is pulled from a rear portion toward a front portion of the tongue. Channel 84 extends from the top of head 6 to the front of head 6 along the curve of the front wall of head 6. The channel 84 can be used to distribute chlorhexidine to the user's tongue immediately after the surface of the tongue is scraped. Other antibacterial solutions can be applied. Channel 84 can be a single channel with a single outlet 86 defined by bottom surface 52 of scraping wall 54. Channel 84 can be branched into a plurality of branches or can define a common plenum with a plurality of outlets 86 spaced along bottom surface 52 of wall 54. With outlets 86 defined by bottom surface 52, the liquid is directly applied to the tongue surface to minimize waste. The direct application also minimizes any squirting into the throat which can cause gagging. Locating outlets 86 forward of working edge 50 is desired so that the applied material is not immediately scraped up and then vacuumed by device 2. In another configuration, outlets 86 can be defined by the outer front surface 88 of wall 54 with the outlets angled down to apply liquid directed through the outlets down onto the tongue.

Head 6 defines an elongated port 90 that removably receives a tube from a supply 92 of the material to be distributed through channel 84. The user connects a supply 92 (such as a bottle or a supply tube connected to a pressurized supply of fluid) of the material to port 90 when application of the material is desired. Supply can be carried by handle 4, can be carried by the user, or can be an independent supply having a pump that delivers the material. The supply tube can be long enough for the user to hold the supply bottle 92 in the same hand as the one that holds device 2. One example is to scrape the tongue and apply the antibacterial liquid prior to surgeries. The antibacterial liquid or gel can be held in a small squeeze bottle that is held in the hand with its supply tube extending down the length of handle 4 where it is frictionally received in port 90. The antibacterial liquid or gel can be supplied by a pressurized bulk supply controlled by the user. In another configuration, the liquid can be distributed via gravity through channel or channels 84 with the size of channels 84 limiting the amount of liquid applied. The application of the liquid can be controlled by tipping the device forward to scrape the tongue surface. When the user is finished, the device is pivoted to an upright position where the liquid falls back into its supply bottle. In a situation where devices 2 are disposable and intended for one-time use with patients, the liquid antibacterial material or medicine can be held in a chamber on top of head 6 and applied when device 2 is used and then discarded.

In the configuration of FIG. 9, an intermediate supply device 94 is disposed between first and second valves 96. Device 94 is filled from supply 92 through the first valve 96. This is achieved by applying pressure to supply 92 or with a pump. When the user is ready to dispense the material onto the tongue, the user squeezes device 94 and almost all of the material held within device 94 is dispensed onto the tongue. This allows a controlled volume of material to be dispensed each time device 94 is squeezed. The controlled volume is defined by the size of the chamber defined by device 94. In another configuration, an electric pump is used to meter the material onto the tongue through the head of the device.

FIGS. 17-20 depict another embodiment of device 2 that allows the user to dispense a material onto the tongue. In this configuration, the body of device 2 defines a material outlet 100 through which a material is dispensed onto the tongue.

As described above, the material is, for example, an antibacterial material such as chlorhexidine gluconate, carbamide peroxide, or a mixture of hydrogen peroxide and water; each provided as a liquid or a gel. Material outlet 100 is defined by head 6 on the handle side of trough 60 such that trough 60 is disposed directly between material outlet 100 and wall 54. This location allows the material to be applied to the tongue shortly before being removed by the vacuum when the vacuum is turned on. In this position, the user can draw device 2 across the tongue once or twice with the vacuum on to remove thick debris and loosen the papillae of the tongue. The user can then use device 2 to apply antibacterial material to the tongue. The application of the material can be done with the vacuum on or the vacuum off. This material is then removed before it is swallowed or aspirated. When the material was applied with the vacuum off, another pass of device 2 on the tongue with the vacuum turned on removes the material. When applied with the vacuum on, the material is removed quickly leaving only a trace functional amount or a thin coating of the material on the papillae.

Material outlet 100 is at least a single opening defined by wall 70. Alternatively, as shown in FIG. 19, material outlet 100 is provided in the form of a wide groove extending across head 6 and can be a curved groove defined by wall 70 and disposed parallel to trough 60 that allows the material to be dispensed over a wide strip on the tongue.

Material outlet 100 is in fluid communication with at least one feeder channel 102 that extends up to a material holding chamber 104. The material is delivered to holding chamber 104 through a valve 106 from a compressible supply 108. Supply 108 has an outlet that is received in the end of chamber 104 in front of valve 106. The user squeezes supply 108 to push the material from supply 108 into chamber 104. The material is then directly delivered to outlet 100 or the user releases supply 108 and allows it to fill with air. The user then squeezes supply 108 again to push all of the material out of outlet 100. This configuration of device 2 can be single use and discarded after use. This configuration also allows supply 108 to be removed when it is empty with a replacement supply 108 being reattached to the tool for use with the same person.

Supply 108 is carried by handle 4. Handle 4 defines a recess into which supply 108 is received to stabilize it when the user is compressing supply 108.

Another feature that can be included with any of the above configurations is the addition of a light 110 disposed at head 6. In FIGS. 1-4, light 110 is provided by a small light emitting diode (LED) powered by a battery 112 and controlled with a switch 114. In this configuration, switch 114 is disposed at head 6. Switch 114 can be located at other locations along handle 4. Light 110 can be disposed at the front of wall 54 to shine down on the tongue.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the description and illustration of the invention is an example and the invention is not limited to the exact details shown or described. Modifications and alterations of those embodiments will be apparent to one who reads and understands this general description. The present disclosure should be construed as including all such modifications and alterations insofar as they come within the scope of the appended claims or equivalents thereof. Throughout the description and claims of this specification the words "comprise" and "include" as well as variations of those words, such as "comprises," "includes," "comprising," and "including" are not intended to exclude additives, components, integers, or steps.

The invention claimed is:

1. A tongue cleaning device that is used for removing debris from a tongue, the device comprising:
    a handle and a head that includes a scraping wall that has a handle-facing inner surface, an outer surface disposed substantially opposite the handle-facing inner surface, and a bottom surface extending between the handle-facing inner surface and the outer surface;
    the scraping wall having a working edge that is used to engage the tongue and remove debris from the tongue, the working edge being defined at the junction of the handle-facing inner surface and the bottom surface;
    the head defining a debris-removal vacuum inlet positioned to remove debris when subjected to a vacuum pressure;
    the head defining a fluid distribution through channel having an inlet and at least one outlet, the at least one outlet disposed forward of the working edge such that the working edge is disposed intermediate the at least one outlet and the debris-removal vacuum inlet; and
    a supply of liquid antibacterial material removably connected to the inlet of the fluid distribution through channel, the supply being disposed external to the handle.

2. The device of claim 1, wherein the at least one outlet is defined by the bottom surface of the scraping wall.

3. The device of claim 1, wherein the handle defines a primary vacuum control opening.

4. The device of claim 3, further comprising a cover slidably carried by the handle at the primary vacuum control opening.

5. The device of claim 3, wherein the primary vacuum control opening is in the form of a plurality of spaced-apart openings.

6. The device of claim 3, wherein the primary vacuum control opening is in the form of a narrow slit.

7. The device of claim 3, further comprising a movable cover carried by the handle and movable between open and closed positions with respect to the primary vacuum control opening the closed position of the movable cover completely closing the primary vacuum control opening.

8. The device of claim 3, wherein the handle defines a grip area defining at least one recess; the primary vacuum control opening being defined by the at least one recess of the grip area.

9. The device of claim 8, wherein the primary vacuum control opening is offset forward in the at least one recess of the grip.

10. The device of claim 1, further comprising a vacuum source in communication with the debris-removal vacuum inlet.

* * * * *